United States Patent
Pinchuk

(10) Patent No.: US 12,263,123 B2
(45) Date of Patent: Apr. 1, 2025

(54) GLAUCOMA DEVICE INSERTER

(71) Applicant: INNFOCUS, INC., Miami, FL (US)

(72) Inventor: Leonard Pinchuk, Miami, FL (US)

(73) Assignee: INNFOCUS, INC., Miami, FL (US)

(*) Notice: Subject to any disclaimer, the term of this patent is extended or adjusted under 35 U.S.C. 154(b) by 829 days.

(21) Appl. No.: 17/433,907

(22) PCT Filed: Feb. 20, 2020

(86) PCT No.: PCT/US2020/018940
§ 371 (c)(1),
(2) Date: Aug. 25, 2021

(87) PCT Pub. No.: WO2020/176315
PCT Pub. Date: Sep. 3, 2020

(65) Prior Publication Data
US 2022/0133538 A1 May 5, 2022

Related U.S. Application Data

(60) Provisional application No. 62/811,045, filed on Feb. 27, 2019.

(51) Int. Cl.
*A61F 9/007* (2006.01)
*A61B 17/34* (2006.01)
(Continued)

(52) U.S. Cl.
CPC ...... *A61F 9/00781* (2013.01); *A61B 17/3468* (2013.01)

(58) Field of Classification Search
CPC ............ A61B 17/3468; A61M 1/3655; A61M 25/001; A61M 25/0012; A61M 27/006;
(Continued)

(56) References Cited

U.S. PATENT DOCUMENTS 6,450,984 B1 * 9/2002 Lynch ................. A61M 25/007
604/8
7,220,238 B2 * 5/2007 Lynch ................. A61F 9/00781
604/8
(Continued)

FOREIGN PATENT DOCUMENTS

CN  103284833 A  9/2013
CN  108430404 A  8/2018
(Continued)

OTHER PUBLICATIONS

Taiwan Office Action and Search Report dated Apr. 8, 2024 of Application No. 109106021.
(Continued)

*Primary Examiner* — Guy K Townsend
(74) *Attorney, Agent, or Firm* — Gordon & Jacobson, P.C.

(57) ABSTRACT

An inserter device is provided for use with a glaucoma drainage device including a tube having a proximal end and a distal end with a lumen extending from the proximal end to the distal end. The inserter device includes an elongate member having a distal end defining a stop surface, and a stylus extending beyond the distal end of the elongate member. The stylus is sized and configured to be received within the lumen of the glaucoma drainage device with the stop surface interfacing to and limiting proximal movement of the glaucoma drainage device. The stylus has a first length that extends beyond the stop surface that is less than a second length of a portion of the lumen of the tube of the glaucoma drainage device that extends beyond the stop surface. Systems and methods are also described and claimed.

14 Claims, 7 Drawing Sheets

(51) Int. Cl.
*A61F 9/008* (2006.01)
*A61M 27/00* (2006.01)

(58) Field of Classification Search
CPC .... A61M 2025/0037; A61M 2025/006; A61M 2210/101
See application file for complete search history.

(56) References Cited

U.S. PATENT DOCUMENTS

| | | | | |
|---|---|---|---|---|
| 7,431,709 | B2* | 10/2008 | Pinchuk | A61F 9/00781 604/9 |
| 7,594,899 | B2* | 9/2009 | Pinchuk | A61F 9/00781 604/8 |
| 7,837,644 | B2* | 11/2010 | Pinchuk | A61F 9/00781 604/9 |
| 9,044,301 | B1* | 6/2015 | Pinchuk | A61F 9/007 |
| 9,101,444 | B2* | 8/2015 | Pinchuk | A61F 9/00781 |
| 9,510,973 | B2* | 12/2016 | Wardle | A61F 9/00781 |
| 9,554,940 | B2* | 1/2017 | Haffner | A61F 2/148 |
| 10,010,450 | B2* | 7/2018 | Pinchuk | A61F 9/007 |
| 10,772,762 | B2* | 9/2020 | Pinchuk | A61F 9/007 |
| 10,945,883 | B2* | 3/2021 | Kahook | A61F 9/00781 |
| 11,666,360 | B2* | 6/2023 | Pinchuk | A61B 17/3468 604/8 |
| 2002/0026200 | A1* | 2/2002 | Savage | A61F 9/00781 606/108 |
| 2003/0175324 | A1* | 9/2003 | Robinson | A61K 38/13 424/427 |
| 2003/0220603 | A1* | 11/2003 | Lynch | A61M 25/0068 604/8 |
| 2003/0236483 | A1* | 12/2003 | Ren | A61F 9/00781 606/107 |
| 2004/0024453 | A1* | 2/2004 | Castillejos | A61F 9/00781 623/4.1 |
| 2004/0210185 | A1* | 10/2004 | Tu | A61F 9/0017 604/27 |
| 2004/0225250 | A1* | 11/2004 | Yablonski | A61F 9/00781 604/8 |
| 2005/0277864 | A1* | 12/2005 | Haffner | A61F 9/00781 604/8 |
| 2005/0283108 | A1* | 12/2005 | Savage | A61F 9/00781 604/8 |
| 2006/0173397 | A1* | 8/2006 | Tu | A61F 9/00781 604/8 |
| 2007/0276316 | A1* | 11/2007 | Haffner | A61F 9/00781 604/8 |
| 2007/0293807 | A1* | 12/2007 | Lynch | A61F 9/00781 604/8 |
| 2008/0015488 | A1* | 1/2008 | Tu | A61F 9/00781 604/27 |
| 2010/0114309 | A1* | 5/2010 | de Juan, Jr. | A61F 9/00772 623/6.62 |
| 2011/0144559 | A1* | 6/2011 | Lafdi | A61L 29/02 604/8 |
| 2011/0319806 | A1* | 12/2011 | Wardle | A61F 9/00781 604/8 |
| 2012/0203262 | A1* | 8/2012 | Connors | A61F 2/06 606/192 |
| 2012/0323159 | A1* | 12/2012 | Wardle | A61F 9/00781 604/8 |
| 2013/0184631 | A1* | 7/2013 | Pinchuk | A61F 9/007 604/8 |
| 2013/0231603 | A1* | 9/2013 | Wardle | A61F 9/0026 604/8 |
| 2014/0213958 | A1* | 7/2014 | Clauson | A61F 9/00781 604/8 |
| 2014/0248454 | A1* | 9/2014 | Lafdi | A61M 25/0043 427/2.3 |
| 2014/0249463 | A1* | 9/2014 | Wardle | A61F 9/00781 604/8 |
| 2014/0371651 | A1* | 12/2014 | Pinchuk | A61F 9/00781 606/108 |
| 2015/0005689 | A1* | 1/2015 | Horvath | A61F 9/00781 604/8 |
| 2015/0148729 | A1* | 5/2015 | Pinchuk | A61M 27/002 604/8 |
| 2015/0257932 | A1* | 9/2015 | Pinchuk | A61F 9/00781 604/8 |
| 2017/0281409 | A1* | 10/2017 | Haffner | A61K 9/0051 |
| 2018/0140462 | A1* | 5/2018 | Pinchuk | A61F 9/007 |
| 2020/0138629 | A1* | 5/2020 | Kahook | A61F 9/00781 |
| 2021/0030590 | A1* | 2/2021 | Blanda | A61F 9/0026 |
| 2021/0045772 | A1* | 2/2021 | Pinchuk | A61B 17/3468 |
| 2021/0330499 | A1* | 10/2021 | Wardle | A61F 9/00781 |
| 2022/0054314 | A1* | 2/2022 | Van Meter | A61B 3/16 |
| 2022/0133538 | A1* | 5/2022 | Pinchuk | A61F 9/0008 604/8 |

FOREIGN PATENT DOCUMENTS

| | | |
|---|---|---|
| JP | 2017-136098 A | 8/2017 |
| TW | 201206406 A | 2/2012 |
| WO | 2018/044684 A1 | 3/2018 |

OTHER PUBLICATIONS

India Exam Report dated Aug. 1, 2023 of Application No. 202147038020.
Japanese Office Action dated Feb. 6, 2024 of Application No. JP2021-550028.
Search Report and Written Opinion dated May 11, 2021 of application No. PCT/US2020/018940.
EP Supplemental Search Report dated Oct. 13, 2022 of application No. EP 20 762 130.1.
Chinese Office Action dated May 17, 2024 of Application No. 2020800172270.
Japanese Office Action dated Jul. 30, 2024 of Application No. JP2021-550028.
Chinese Office Action dated Nov. 28, 2023 of Application No. 202080017227.0.
Chinese Search report dated of Nov. 28, 2023 of Application No. 202080017227.0.
Chinese Office Action dated Jul. 27, 2024 of Application No. CN2020800172270.

* cited by examiner

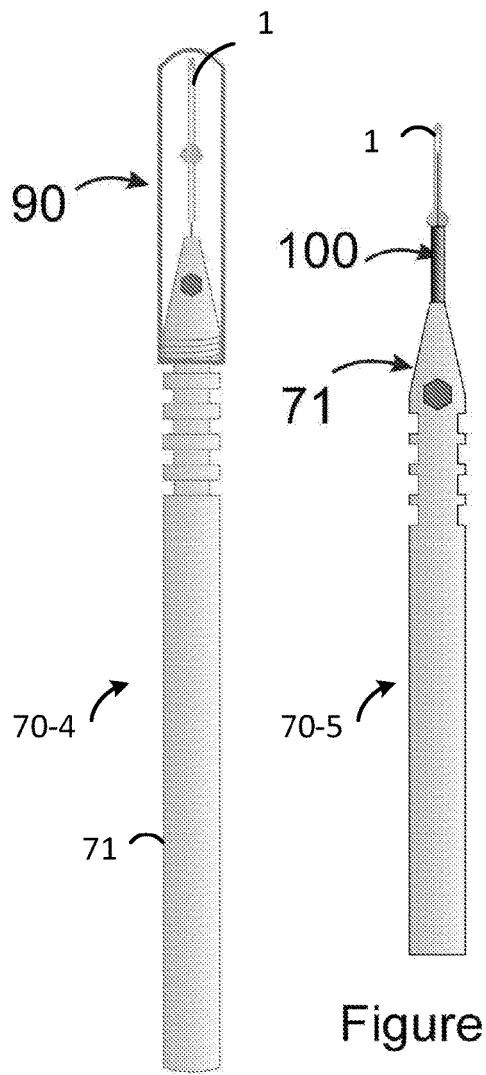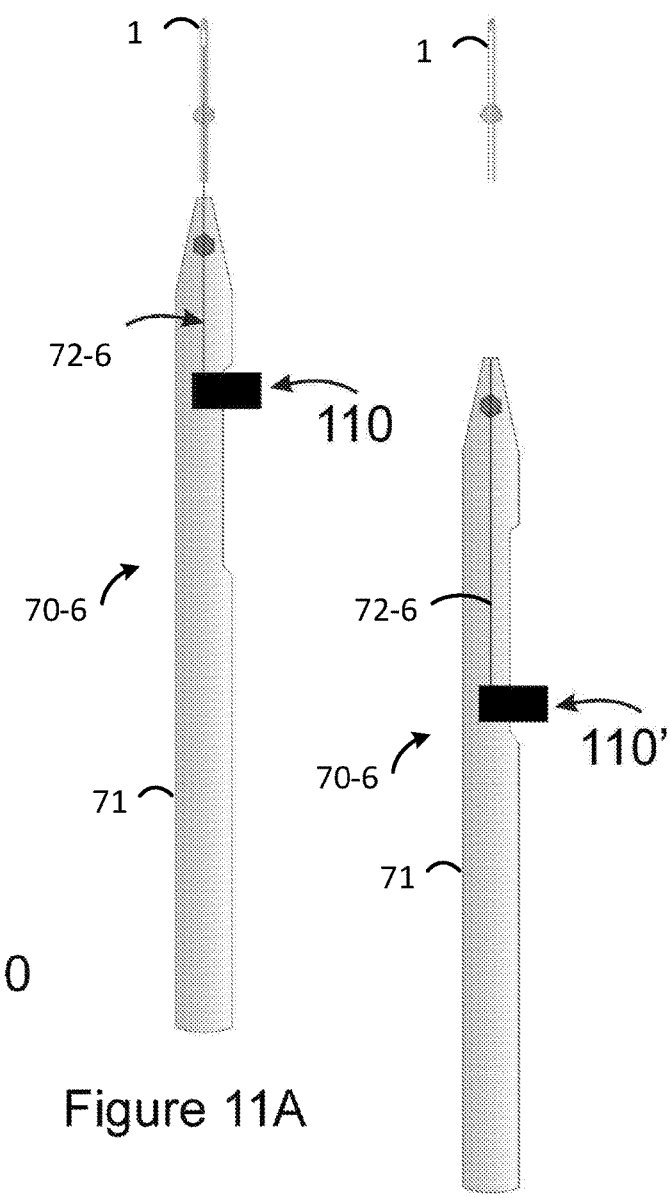
Figure 9
Figure 10
Figure 11A
Figure 11B

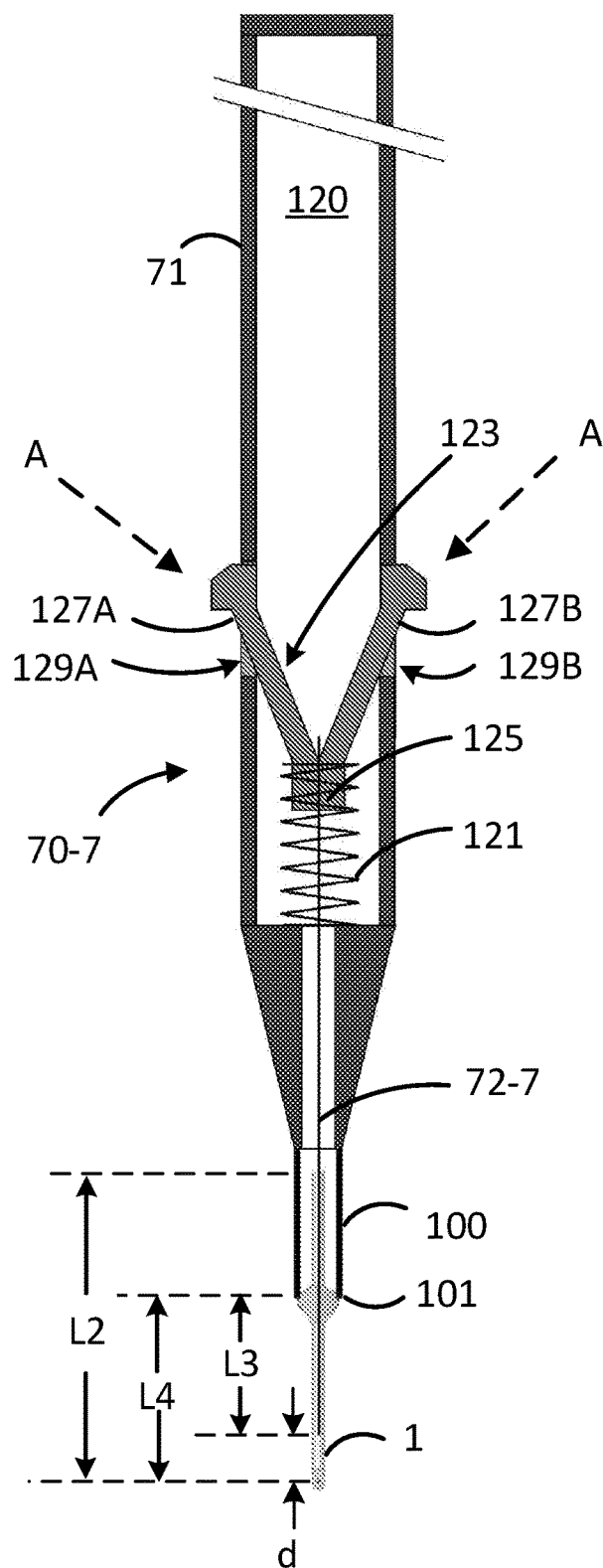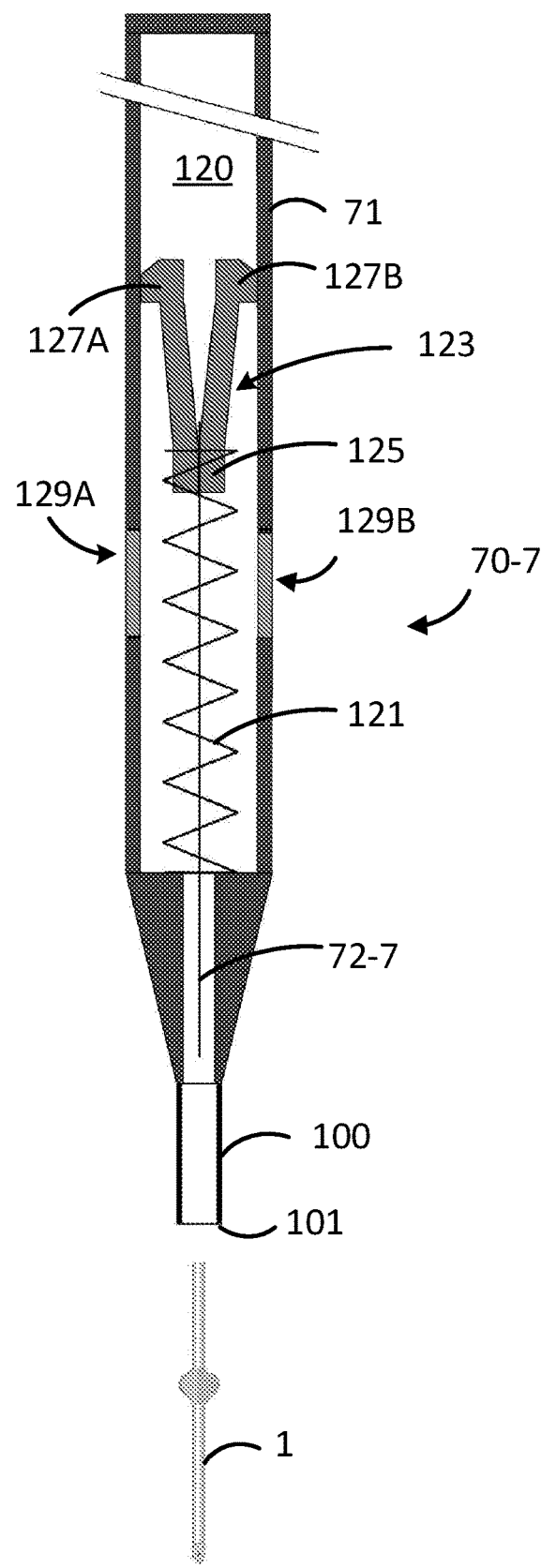
Figure 12A
Figure 12B

GLAUCOMA DEVICE INSERTER

CROSS-REFERENCE TO RELATED APPLICATIONS

This application is the national stage entry of International Application Serial No. PCT/US2020/018940, filed Feb. 20, 2020, which claims priority to U.S. Provisional Application 62/811,045, filed Feb. 27, 2019, the entire contents of which are incorporated herein by reference.

BACKGROUND

InnFocus, Inc. of Miami, Florida has issued patents on glaucoma drainage implants (GDIs) (e.g., U.S. Pat. Nos. 7,431,709, 7,594,899, 7,837,644 and 9,101,444), which are herein incorporated by reference in their entireties. A typical GDI is shown in FIG. 1 and includes an elongated tubular body or tube 1 with a distal end 2 and a proximal end 3. One or more projections or fins 4 extend radially from the exterior surface of the tube 1 at an intermediate position between the distal end 2 and proximal end 3. When the GDI is implanted into the eye, the fin(s) 4 can aid in preventing migration of the tube 1 into the eye. The tube 1 also includes a bevel 6 on the distal end 2. The tube 1 has an internal lumen 5 that extends from the distal end 2 to the proximal end 3. The length of the lumen 5 is labeled L2 in FIG. 1. When the GDI is implanted into the eye, the lumen 5 provides a flow path for drainage of fluid from the interior of the eye (e.g., drainage of aqueous humor from the anterior chamber).

FIG. 2 illustrates an example implantation or placement of the GDI into the eye. In this case, the distal end 2' is in the anterior chamber of the eye and the tube 1' extends under the limbus and through the sclera 10. The proximal end 3' rests in a dissected plane between the conjunctiva/Tenons and the sclera. Fluid (e.g., aqueous humor) from the anterior chamber flows through the lumen 5 of the GDI and drains into the sub-conjunctiva/Tenons space to form a small blister called a bleb. The projection or fin(s) 4' can be located posterior to the limbus and can be buried in a small pocket 11 cut into the sclera with a scalpel or triangular knife. The GDI is typically placed into this position by forming a needle tract (or tissue passageway) through the scleral pocket 11 under the limbus (area 10) and into the anterior chamber. The tube 1' of the GDI can be grasped by forceps and inserted into this needle tract.

The GDI (particularly the tube 1 and possibly the fin(s) 4 of the GDI) is typically made from a soft and flexible material such as poly(styrene-block-isobutylene-block-styrene) (SIBS) of Shore hardness less than 60 A. In embodiments, the GDI can be made from SIBS of Shore hardness in the range 30 A to 50 A, more preferably in the range 35 A to 45 A, and possibly with a Shore hardness of 40 A. In embodiments, the diameter of the lumen 5 of the tube 1 can range from 0.04 mm to 0.1 mm, more preferably in the range 60 µm to 80 µm and can be 70 µm. The outer diameter of the tube 1 can range from 0.2 mm to 0.8 mm and can be 0.35 mm in embodiments. In these embodiments, the soft material and size and the tube 1 on both sides of the fin(s) 4 renders the tube 1 very floppy and thus difficult to push through the needle tract under the limbus and into the anterior chamber.

Implanting the device is traditionally accomplished with forceps which are used to hold the GDI near its proximal tip and incrementally move the GDI through the pocket and needle tract and into the anterior chamber. Problems with forceps is that the GDI needs to be held very carefully so as not to inadvertently squeeze the lumen closed, which can take tens of minutes to spring back open. In addition, the GDI is very small and it can be dropped. Further, the surgeon needs to lift his/her eyes from the surgical microscope to accept the GDI from the scrub nurse which is non-optimum. Lastly, the GDI does not always pass through the needle tract due to obstruction of the needle tract by fibrous strands and the like. In short, implanting the GDI with forceps is clumsy and not optimum. There is a need for a quicker and more reliable method of handling and implanting the GDI.

SUMMARY

The present disclosure describes an inserter that is used to support a soft flexible GDI when packaged, sterilized and shipped as well as to facilitate implanting the GDI into the eye. It is contemplated that the GDI and inserter will be packaged as a glaucoma system or kit with the GDI supported by the stylus of the inserter as described herein.

BRIEF DESCRIPTION OF THE DRAWINGS

FIGS. 9, 10, 11A, 11B, 12A and 12B show alternate embodiments of inserters similar to the inserter of FIG. 7D.

DESCRIPTION OF ILLUSTRATIVE EMBODIMENT(S)

In this disclosure, the term "proximal" refers to a position closer to the surgeon implanting the device, and "distal" refers to a position away from the surgeon implanting the device.

The present disclosure describes an inserter that enables a soft flexible GDI to be inserted into a needle tract (or tissue passageway) that leads to the anterior chamber of the eye with the distal end 2 of the GDI in the anterior chamber of the eye. The inserter includes a stylus that is located within and received by the lumen 5 of the GDI. The stylus functions to support and carry the GDI as the GDI is inserted into and through the needle tract. For the purpose of this disclosure, the stylus can be a wire, a guidewire, a stylet, a stiffener, and the like and for simplicity will simply be referred to as a stylus. Further, in order to fit into the lumen 5 of GDI, the maximal outer diameter of the stylus can be smaller than the inner diameter (or lumen) of the GDI, which can be 60 to 80 µm in embodiments. Examples of materials that can comprise the stylus are stainless steel, cobalt-chromium-nickel compounds (Elgiloy), Nitinol, tungsten, and the like. In embodiments the material comprising the stylus is relatively stiff (as compared to the flexible material of the tube of the GDI), non-corrosive and biocompatible.

Figure 2:
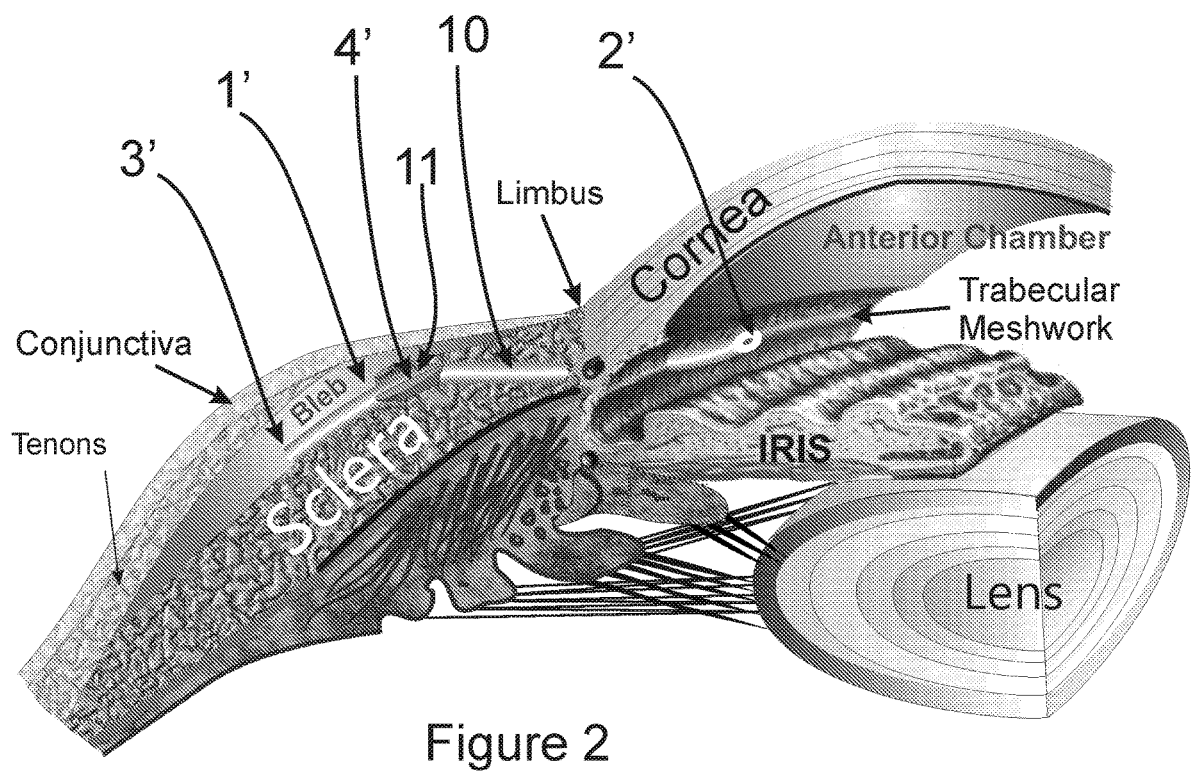
FIG. 2 is a diagram that shows an example implantation or placement of the GDI of FIG. 1 into the eye.
Figure 3:
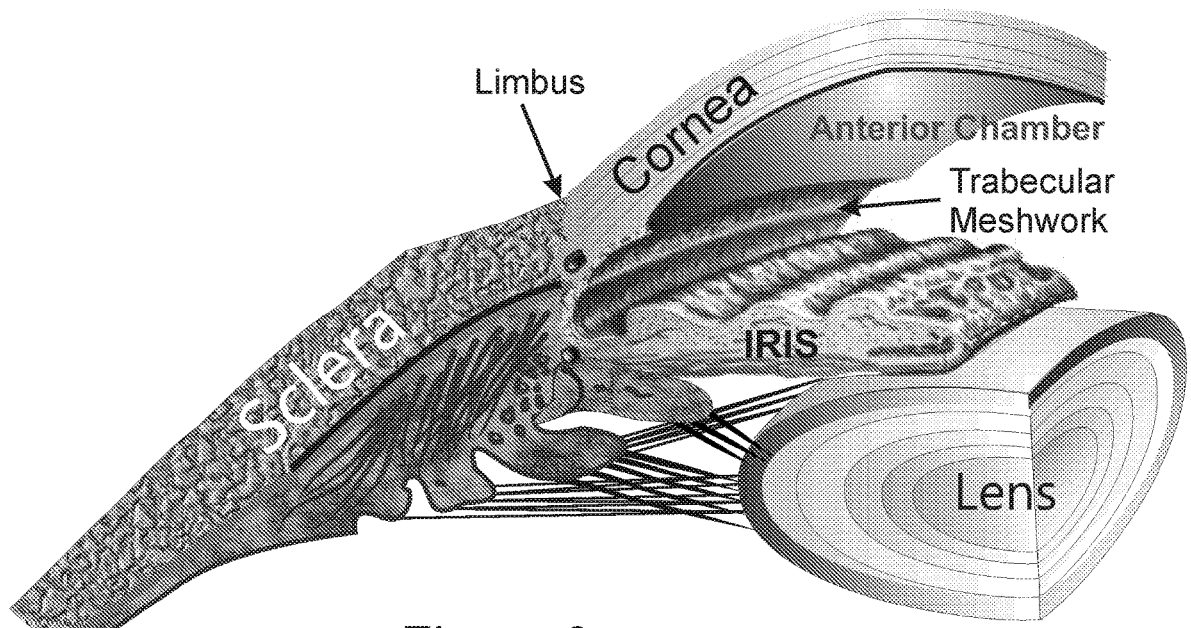
FIG. 3 is a diagram that illustrates anatomical structures or parts of the eye.
Figure 4:
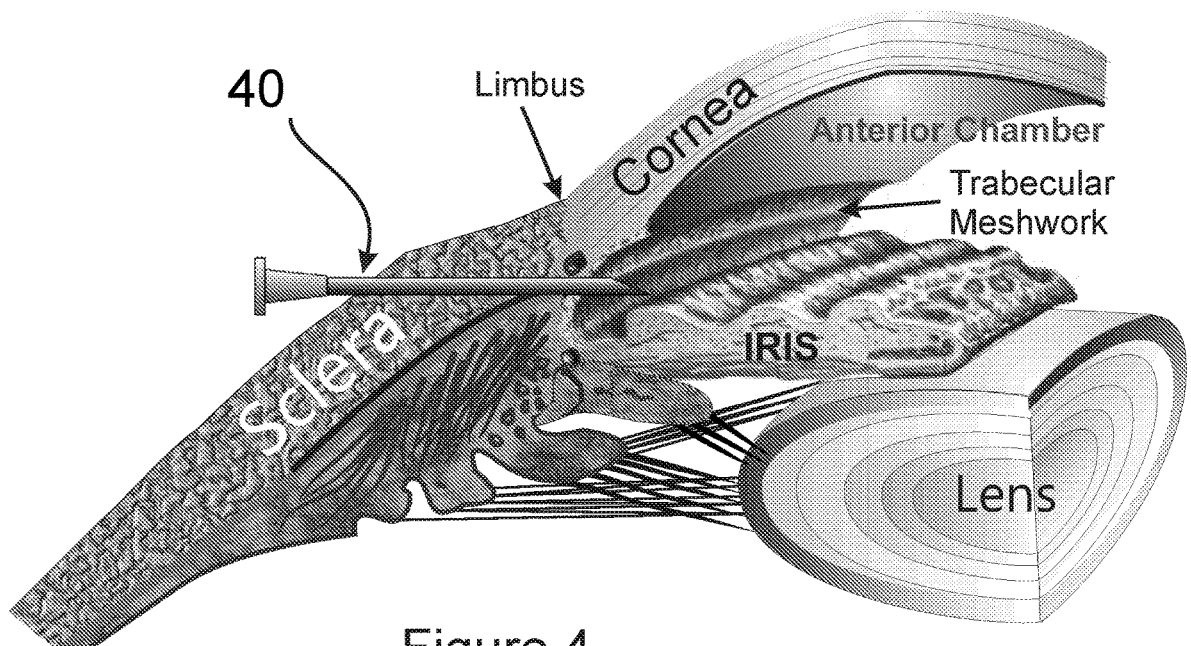
FIG. 4 is a diagram that shows a needle forming a needle tract (or tissue passageway) under the limbus and to the anterior chamber of the eye.

FIG. 3 is similar to FIG. 2 except the conjunctiva, Tenon's capsule, bleb and GDI are omitted for ease of illustration. In order to insert the GDI under the limbus with its distal end in the anterior chamber of the eye, a needle 40 is used to form a needle tract (or tissue passageway) under the limbus and to the anterior chamber as shown in FIG. 4. As is often the case, the formation of the needle tract is preceded by formation of a small pocket in the sclera, using a scalpel or triangular knife, which eventually will house the fin(s) 4 of the GDI. It is customary in surgery of this nature to instruct the patient to look down or up in order to expose more sclera to facilitate forming the needle tract and implanting the device. It is also necessary at times to place a traction suture (not shown) through a partial thickness of the cornea such that the surgeon can rotate the eye by pulling on the traction suture to facilitate exposure of the sclera. When the tissue under the limbus is stressed in these manners, and a needle forced through it, is common for the needle tract thus formed when the needle 40 is removed and the eye relaxed, to be curved rather than in a straight line.

Figure 5:
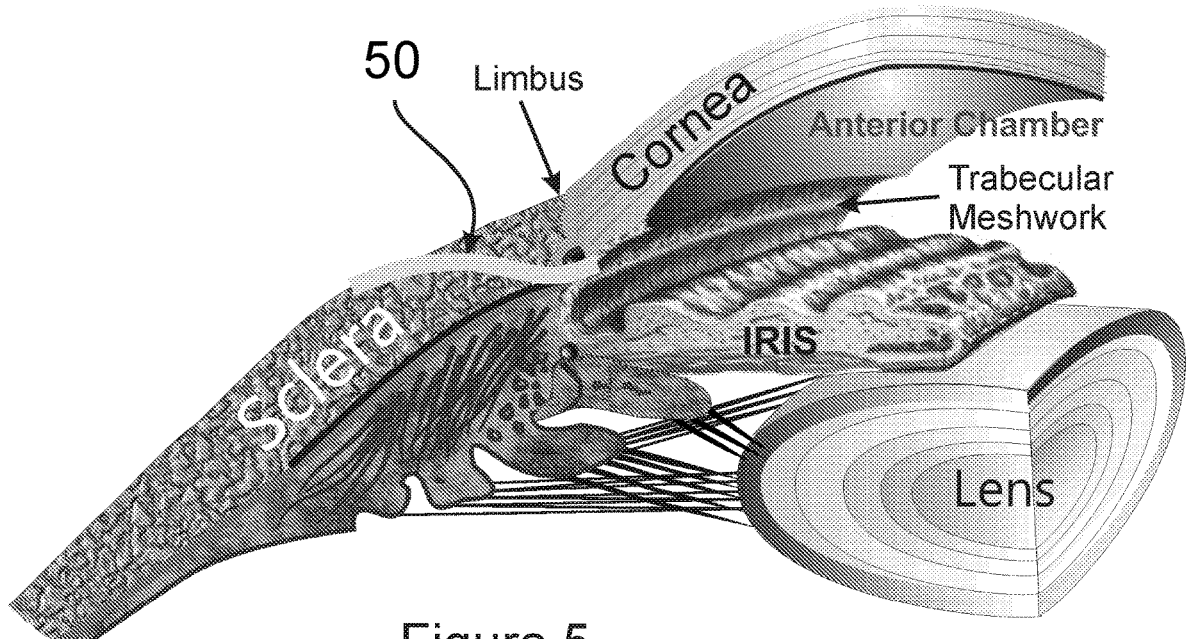
FIG. 5 is a diagram showing the needle tract formed by the needle of FIG. 4.

FIG. 5 shows a needle tract 50 thus formed as a curved tract, and it is this curved needle tract 50 that renders it difficult to use a traditional stylus to facilitate placing the GDI in the needle tract as will be explained below.

Figure 1:
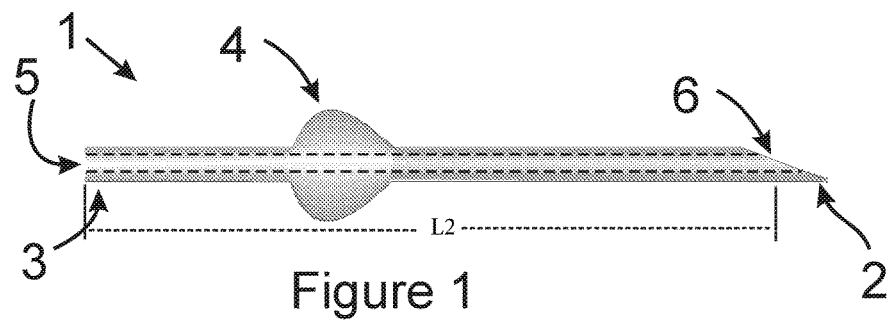
FIG. 1 is a cross-sectional schematic diagram of a prior art GDI.
Figure 6:
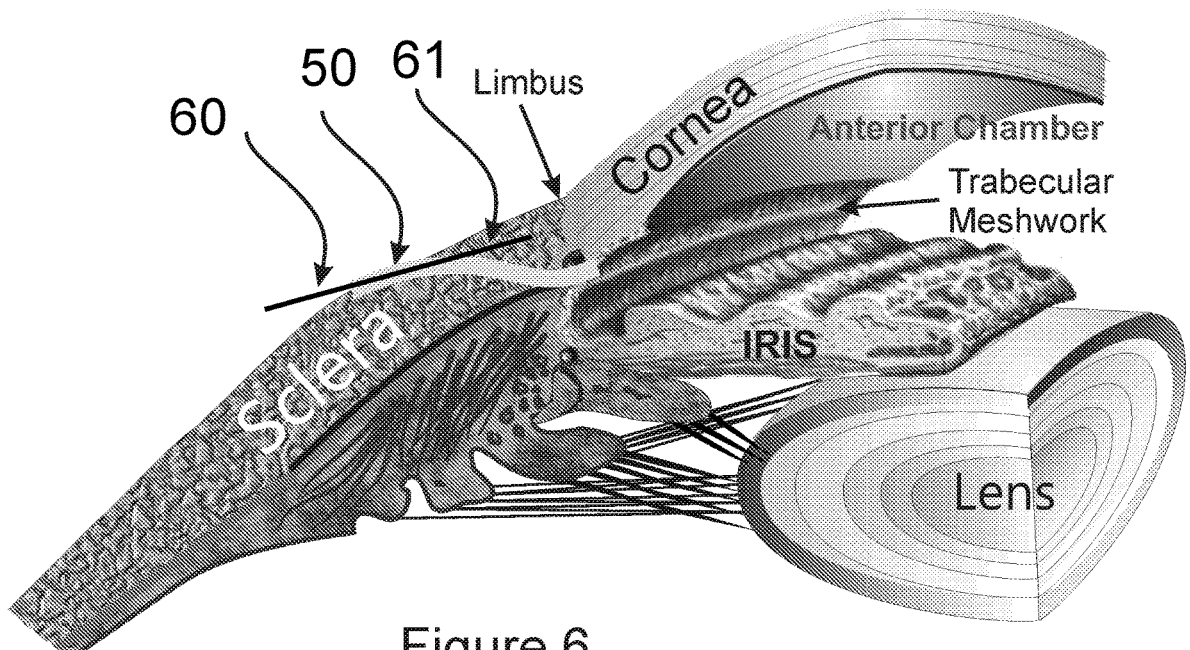
FIG. 6 is a diagram showing the insertion of a stylus into the needle tract of FIG. 5.

FIG. 6 shows a stylus 60 with a distal end 61. Stylus 60 is sufficiently thin to slidely fit into lumen 5 of the GDI (see FIG. 1). The maximal outer diameter of the stylus 60 can be approximately 10% to 30% smaller than the diameter of the lumen 5 of the GDI. For example, where the diameter of the lumen 5 of the GDI is in the range of 60 µm to 80 µm, the maximal outer diameter of the stylus 60 can be in the range of 42 µm to 72 µm. The stylus can be a straight wire or tapered along its length. Note that a thin stylus of this dimension can have a sharp distal end, and if made sufficiently stiff to allow pushability, the stylus 60 will not follow the needle tract 50; instead, it will penetrate the tissue adjacent to the needle tract at a bend as is shown by the distal section 61 of stylus 60 which is protruding into sclera.

Figures 7A, 7B, 7C, 7D:
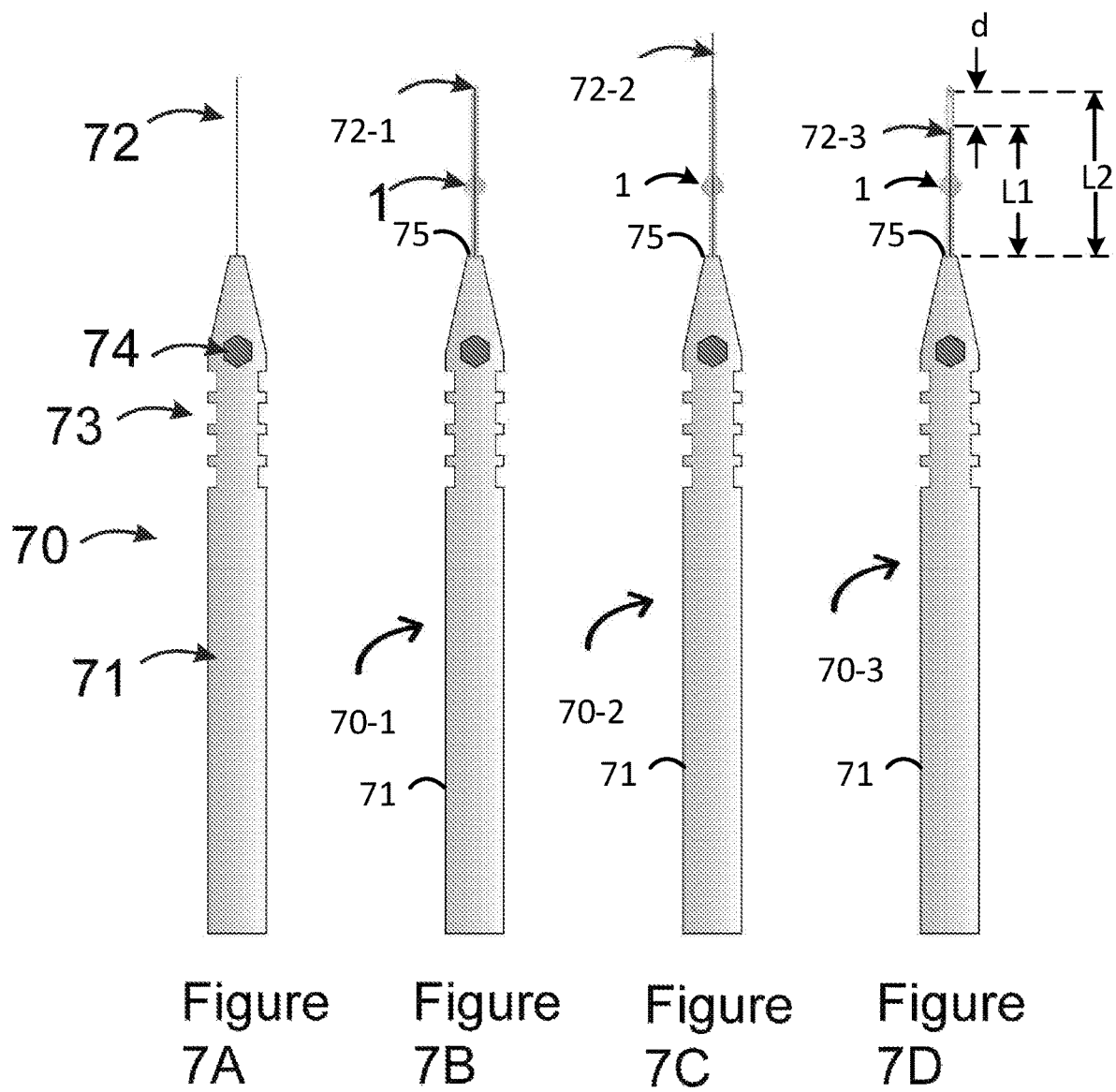
FIG. 7A is a diagram showing an inserter having a stylus for supporting and carrying the GDI of FIG. 1.
FIG. 7B is a diagram showing an inserter having a stylus that supports and carries the GDI of FIG. 1 where the stylus is sized and configured to extend to the distal end of the GDI.
FIG. 7C is a diagram showing an inserter having a stylus that supports and carries the GDI of FIG. 1 where the stylus is sized and configured to extend well beyond the distal end of the GDI.
FIG. 7D is a diagram showing an inserter having a stylus that supports and carries the GDI of FIG. 1 where the stylus is sized and configured such that the distal end of the stylus is offset proximally by a distance "d" relative to the distal end of the GDI.

FIG. 7A shows an inserter 70, which includes a handle 71, a stylus 72 that extends from the distal end of the handle 71, optional grips 73 and optional orientation marker 74. Orientation marker 74 is aligned with the plane of the bevel 6 at the distal end 2 of the GDI to indicate to the surgeon where the plane of the bevel 6 is as it is required that the bevel face the cornea. For example, the surgeon can be instructed to position the GDI on the stylus 72 such that the bevel 6 is on the same plane as the orientation marker 74 before inserting the GDI into the tissue tract. In this example, the stylus 72 is rigidly fixed to handle 71. In embodiments, the GDI can remain positioned on the stylus 72 due to friction between the internal lumen wall of the GDI and the stylus 72. Such friction can also limit or reduce rotation movement of the GDI about the stylus 72.

FIG. 7B shows an inserter 70-1 with a stylus 72-1 whose length is configured to match the length of the lumen 5 of the tube 1 of the GDI. In this configuration, the distal end 75 of the handle 71 provides a stop surface that interfaces to the proximal end 3 of the tube 1 of the GDI when the stylus 72-1 is received within the lumen 5 of the tube 1 of the GDI. With the proximal end 3 of the tube 1 of the GDI butting up against the stop surface provided by the distal end 75 of the handle 71, the stylus 72-1 extends within the lumen 5 of the tube 1 of the GDI to approximately the beveled distal end 2 of the GDI. This configuration of stylus 72-1 cannot be used to effectively insert the GDI into the needle tract as the GDI is very soft and it will accordion in the area of the distal end 2 when entering the needle tract 50 and expose the stylus 72-1 which will stick into tissue and not follow the needle tract 50 as explained above relative to FIG. 6.

FIG. 7C shows an inserter 70-2 with a stylus 72-2 whose length is configured to be greater than the length of the lumen 5 of the tube 1 of the GDI. In this configuration, the distal end 75 of the handle 71 provides a stop surface that interfaces to the proximal end 3 of the tube 1 of the GDI when the stylus 72-2 is received within the lumen 5 of the tube 1 of the GDI. With the proximal end 3 of the tube 1 of the GDI butting up against the stop surface provided by the distal end 75 of the handle 71, the stylus 72-2 extends within the lumen 5 of the tube 1 of the GDI well beyond the beveled distal end 2 of the GDI and thus protrudes from the distal end 2 of the GDI. This configuration of stylus 72-2 cannot be used to effectively insert the GDI into the needle tract as the distal portion of the stylus 72-2 that extends beyond the beveled distal end 2 of the GDI will stick into tissue and not follow the needle tract 50 as explained above relative to FIG. 6.

FIG. 7D shows an inserter 70-3 with a stylus 72-3 whose length L1 is configured to be less than the length L2 of the lumen 5 of the tube 1 of the GDI. In this configuration, the distal end 75 of the handle 71 provides a stop surface that interfaces to the proximal end 3 of the tube 1 of the GDI (when the stylus 72-3 is received within the lumen 5 of the tube 1 of the GDI) and that functions to limit proximal movement of the GDI. With the proximal end 3 of the tube 1 butting up against the stop surface provided by the distal end 75 of the handle 71, the length L1 of the stylus 72-3 extends within the lumen 5 of the tube 1 of the GDI to approximately 1 mm proximal to the distal end 2 of the GDI. This configuration of stylus 72-3 can be used to effectively insert the GDI into the needle tract as the distal portion of the GDI that extends beyond the distal end of the stylus 72-3 can follow the needle tract as the soft tube 1 of the GDI cannot penetrate tissue and can bend to follow the needle tract. This finding was not at all obvious.

Figure 8:
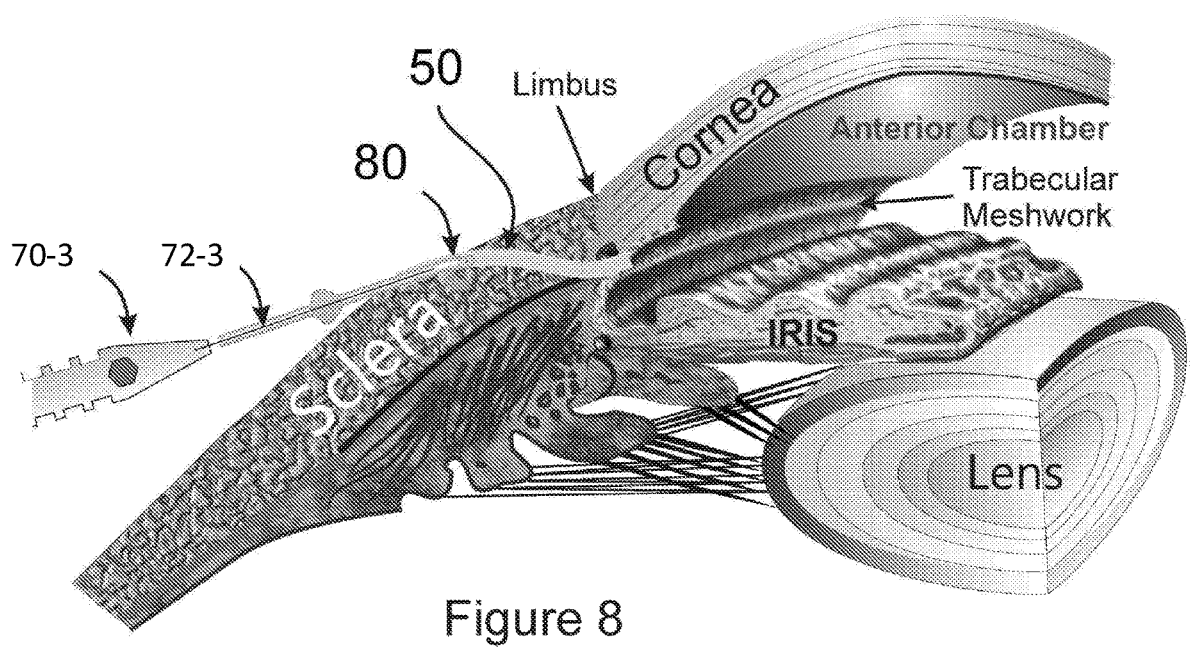
FIG. 8 is a diagram showing the inserter of FIG. 7D being used to insert the GDI of FIG. 1 supported and carried on the stylus of the inserter into and through the needle tract of FIG. 5.

Note that the stylus 72-3 can be sufficiently stiff to allow rigidity of the GDI during insertion of the GDI into and through the needle tract. The stylus 72-3 can also be sufficiently short to not restrict the GDI from following the contour of the needle tract. This maneuver is shown in FIG. 8 where the distal tip 80 of the tube 1 of the GDI bends in the needle tract 50 and the stylus 72-3 of the inserter 70-3 provides the rigidity to allow insertion of the GDI through the needle tract to proceed. Once the GDI is in place, as is shown in FIG. 2, the stylus 72-3 can simply be withdrawn or retracted from the lumen 5 of the GDI leaving the GDI behind in the needle tract. This maneuver may be facilitated by holding the GDI in place with forceps as the stylus 72-3 of the inserter 70-3 is withdrawn or retracted from the lumen 5 of the tube 1 of the GDI.

Note that the length L1 of the stylus 72-3 is configured to be less than the length L1 of the full lumen 5 of the tube 1 of the GDI that extends from the stop surface defined by the distal end 75 of the handle 71. In this configuration, with the proximal end 3 of the tube 1 of the GDI butting up against the stop surface provided by the distal end 75 of the handle 1, the distal end of the stylus 72-3 is displaced from the distal tip of the GDI at a displacement or distance "d" as shown in FIG. 7D. The displacement "d" can be determined by the difference between the full length L2 of the lumen 5 of the tube 1 of the GDI and the smaller length L1 of the stylus 72-3 as shown in FIG. 7D. In embodiments, the displacement "d" (and thus the difference between L2 of the tube lumen and L1 of the stylus 72-3) is in the range of 0.5 to 3 mm, preferably 1 to 2 mm. It is also possible to apply a lubricant in the lumen 5 of the GDI to facilitate sliding of the stylus in the lumen 5 of the GDI. Exemplary lubricants include but are not limited to glycerin, hyaluronic acid and methylcellulose.

FIGS. 9-12B show alternate embodiments of inserters similar to the inserter of FIG. 7D.

FIG. 9 shows an embodiment of an inserter 70-4 similar to FIG. 7D with a removable and disposable cap 90 that can be placed over the GDI and the distal portion of the handle 71 of the inserter 70-4. The cap 90 can be designed with cutouts or loose tolerances to allow for ethylene oxide sterilization and can be removed for use.

FIG. 10 shows an embodiment of an inserter 70-5 similar to FIG. 7D with a rigid over-tube 100 rigidly attached to handle 71 of the inserter 70-5, which can add additional support to the stylus of the inserter to help pushability. The over-tube 100 can be made from metallic hypodermic tubing or can be plastic made from polyester, Delrin, Nylon, Teflon, polyimide, polysulfone, and the like. It is also envisaged that the over-tube 100 can receive and surround the proximal portion of the GDI and can push against the fin(s) 4 of the GDI to facilitate pushability of the GDI during insertion of the GDI into and through the needle tract as described herein. Note that while the distal end of the tube 100 pushes against the fins (4) of the GDI during insertion of the GDI into and through the needle tract, the stylus provides rigidity to the GDI in order to reduce or limit the possibility that the distal end of the stylus will penetrate the wall of the tube of the GDI during insertion.

FIGS. 11A and 11B show an embodiment of an inserter 70-6 similar to FIG. 7D with a retractable stylus 72-6. Stylus 72-6 is rigidly attached to a thumb slide 110. When the GDI is in place (FIG. 11A), the user can retract the thumb slide 110 (relative to the handle 71) in the proximal direction as is shown in FIG. 11B, and the stylus 72-6 is retracted such the stylus 72-6 moves proximally relative to the GDI and the stylus 72-6 is removed from the lumen 5 of the tube 1 of the GDI with the GDI in place as shown. A lock (not shown) may be incorporated into the inserter 70-6 shown in FIGS. 11A and 11B to lock the slide 110 (relative to the handle 71) in its unactivated (unretracted) position shown in FIG. 11A. The lock is configured to prevent the slide 110 from moving during transit of the inserter 70-6. At the time of use of the inserter 70-6, the lock can be removed or otherwise displaced to unlock the slide 110. In embodiments, the lock can take the form of a pin that is configured to selectively traverse and engage the slide 110 and the wall of the handle 71 to lock the slide 110. Such pin can be selectively removed or displaced from one or both of the slide 110 and the wall of the handle 71 to unlock the slide 110 to permit the user to move the slide 110 relative to the handle 71. Also, in embodiments, the lock can be a piece of material that fits into a tract in which the slide 110 moves to prevent the slide 110 from retracting or otherwise moving relative to the handle 71 (akin to a piece of wood used to prevent sliding doors from opening). At the time of use of the inserter 70-6, such piece of material can be removed from the tract to permit the user to move the slide 110 in the tract.

FIGS. 12A and 12B show an embodiment of an inserter 70-7 similar to FIGS. 7D, 10 and 11 with a retractable stylus 72-7 that is spring-loaded such the stylus 72-7 moves proximally relative to the GDI and the stylus 72-7 is removed from the lumen 5 of the tube 1 of the GDI with the GDI in place simply by spring activation. In this embodiment, the handle 71 has an interior chamber 120 that house a spring 121 at its proximal end. The spring 121 interfaces to a wish-bone actuator 123 that can slide or move proximally in the interior chamber 120 under user control. The actuator 123 has a proximal base 125 and opposed arms 127A, 127B. The proximal end of the stylus 72-7 is rigidly secured or captured by the base 125 of the actuator.

In a spring-loaded configuration of the inserter 70-7 shown in FIG. 12A, the arms 127A and 127B of the actuator 123 extend distally from the base 125 through corresponding slots 129A, 129B in the handle 71 to exterior space. The arms 127A, 127B butt up against the proximal ends of the corresponding slots 129A, 129B and hold the actuator 123 in place with the spring 121 in a compressed state. In the spring-loaded configuration of the inserter 70-7, the distal portion of the stylus 72-7 that extends through the overtube 100 and beyond the distal end 101 of the overtube 100 can support the GDI. Specifically, the distal portion of the stylus 72-7 can be inserted into the lumen 5 of the tube 1 of the GDI such that the distal portion of the stylus 72-7 extends within the lumen 5 of the tube 1 of the GDI as shown. In this configuration, the distal end 101 of the overtube 100 provides a stop surface that interfaces to the fin(s) 4 of the GDI (when the stylus 72-7 is received within the lumen 5 of the tube 1 of the GDI) and that functions to limit proximal movement of the GDI.

With the inserter 70-7 in its spring-loaded configuration, the user/operator can apply manual forces by hand/finger pressure that pushes the arms 127A and 127B of the actuator 123 radially inward (which is shown by arrows labelled A) and releases the arms 127A, 127B from their engagement with the proximal ends of the corresponding slots 129A, 129B. Such actions can release the actuator 123 and allow the compressed spring 123 to expand whereby the spring forces of the compressed spring 123 move or slide the actuator 123 proximally within the chamber 123 as shown in the spring-released configuration of the inserter 70-7 shown in FIG. 12B. Note that with the actuator 123 connected to the stylus 72-7, the proximal movement of the actuator 123 moves or retracts the stylus 72-7 proximally such that the distal portion of the stylus 72-7 is removed from the lumen 5 of tube 1 of the GDI as is evident from FIG. 12B.

As shown in FIG. 12A, the length L3 of the stylus 72-7 that extends beyond the stop surface provided by the distal tip 101 of the overtube 100 is configured to be less than the length L4 of the portion of the lumen 5 of the tube 1 of the GDI that extends beyond the stop surface provided by the distal tip 101 of the overtube 100. With the inserter 70-7 in its spring-loaded configuration and the distal portion of the stylus 72-7 inserted into the lumen 5 of the tube 1 of the GDI such that the distal portion of the stylus 72-7 extends within the lumen 5 of the tube 1 of the GDI as shown, the distal end of the stylus 72-7 is displaced from the distal tip of the GDI at a displacement or distance "d" as shown in FIG. 12A. The displacement "d" can be determined by the difference between the length L4 of the portion of the lumen 5 of the tube 1 of the GDI that extends beyond the stop surface provided by the distal tip 101 of the overtube 100 and the smaller length L3 of the stylus 72-7 that extends beyond the stop surface provided by the distal tip 101 of the overtube 100 as shown in FIG. 12A. In embodiments, the displacement "d" (and thus the difference between L4 of the tube lumen and L3 of the stylus 72-7) is in the range of 0.5 to 3 mm, preferably 1 to 2 mm. It is also possible to apply a lubricant in the lumen 5 of the GDI to facilitate sliding of the stylus in the lumen 5 of the GDI. Exemplary lubricants include but are not limited to glycerin, hyaluronic acid and methylcellulose.

In embodiments, the stylus of the inserter can be formed from drawn wire where the amount of drawdown determines its hardness. The wire should be sufficiently hard but not too brittle to avoid breaking if bent slightly. Various manufacturing methods can be used to fabricate and assembly the handle and stylus assembly of the inserter. For example, the handle can be injection molded with a hole on the distal end sized to accommodate the stylus. The stylus can be cut to a predetermined length and electropolished. The cut length can be dipped in a UV-cured adhesive, inserted into the hole in the handle and then irradiated with UV light until cured. The GDI can then be mounted on the stylus and the bevel 6 of the GDI oriented to align with the orientation marker on the handle.

In embodiments, the inserter with stylus and the GDI can be packaged as a glaucoma system or kit with the GDI supported by the stylus of the inserter. In this case, the stylus can be located within and received by the lumen 5 of the tube 1 of the GDI as shown in FIGS. 7D and 12A.

The inserter configurations and GDI as described herein, with or without a cap (FIG. 9, 90), can easily be placed in a blister package and sterilized according to normal sterilization procedures, preferably ethylene oxide. The fact that the stylus is of smaller diameter than the lumen of the GDI allows ethylene oxide to penetrate the length of the lumen. Furthermore, the inserter configuration and GDI as described herein can be removed from the package and handed to the surgeon without the surgeon looking up from the surgical microscope. The orientation mark 74 of the inserter will indicate what side is bevel (6) up and the surgeon can simply insert the device into and through the needle tract to deploy the GDI into the desired implanted position as described herein.

There have been described and illustrated herein several embodiments of a glaucoma device inserter. While particular embodiments have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. An inserter device for use with a glaucoma drainage device including a tube having a proximal end and a distal end with a lumen extending from the proximal end to the distal end, and at least one protrusion that extends radially from the tube of the glaucoma drainage device at an intermediate position between the proximal end and distal end of the tube of the glaucoma drainage device, the inserter device comprising:

an elongate handle member having an over-tube that is configured to receive and surround a proximal portion of the glaucoma drainage device, wherein the over-tube has a distalmost end that defines a stop surface; and a stylus extending beyond the distal end of the elongate handle member, wherein the stylus is sized and configured to be received within the lumen of the glaucoma drainage device with the stop surface interfacing to and limiting proximal movement of the glaucoma drainage device, and wherein the stylus has a first length that extends beyond the stop surface that is less than a second length of a portion of the lumen of the tube of the glaucoma drainage device that extends beyond the stop surface in use;

wherein the stop surface defined by the distalmost end of the over-tube interfaces to the at least one protrusion of the glaucoma drainage device to limit proximal movement of the glaucoma drainage device.

2. An inserter device according to claim 1, wherein difference between the first length of the stylus and the second length of the lumen portion of the tube of the glaucoma drainage device is in the range of 0.5 to 3 mm.

3. An inserter device according to claim 1, wherein difference between the first length of the stylus and the second length of the lumen portion of the tube of the glaucoma drainage device is in the range of 1 to 2 mm.

4. An inserter device according to claim 1, wherein at least part of the stylus is sized and configured to slide within the lumen of the tube of the glaucoma drainage device.

5. An inserter device according to claim 1, further comprising a lubricant that facilitates sliding movement of the stylus within the lumen of the glaucoma drainage device.

6. An inserter device according to claim 1, wherein the stylus has a maximum outer diameter that is 10% to 30% smaller than diameter of the lumen of the tube of the glaucoma drainage device.

7. An inserter device according to claim 1, wherein the diameter of the lumen of the tube of the glaucoma drainage device is in the range of 60 μm to 80 μm, and the stylus has a maximum outer diameter in the range of 42 μm to 72 μm.

8. An inserter device according to claim 1, wherein the stylus is made from a relatively stiff and rigid material, and the tube of the glaucoma drainage device is made from a relatively soft and flexible material.

9. An inserter device according to claim 8, wherein the material of the stylus is selected from the group consisting of stainless steel, cobalt-chromium-nickel compounds (Elgiloy), Nitinol, tungsten, and the like.

10. An inserter device according to claim 8, wherein the material of the tube of the glaucoma drainage device is poly(styrene-block-isobutylene-block-styrene) (SIBS) of Shore hardness less than 60 A.

11. An inserter device according to claim 1, wherein the elongate handle member includes an orientation marker that is aligned with a bevel on the distal end of the tube of the glaucoma drainage device.

12. An inserter device according to claim 1, wherein the stylus is retractable by operation of inserter device such that the stylus moves proximally relative to the glaucoma drainage device to remove the stylus from the lumen of the tube of the glaucoma drainage device.

13. An inserter device for use with a glaucoma drainage device including a tube having a proximal end and a distal end with a lumen extending from the proximal end to the distal end, the inserter device comprising:

an elongate handle member having a distal end that defines a stop surface;

a stylus extending beyond the distal end of the elongate handle member, wherein the stylus is sized and configured to be received within the lumen of the glaucoma drainage device with the stop surface interfacing to and limiting proximal movement of the glaucoma drainage device, and wherein the stylus has a first length that extends beyond the stop surface that is less than a second length of a portion of the lumen of the tube of the glaucoma drainage device that extends beyond the stop surface in use; and a lubricant that facilitates sliding movement of the stylus within the lumen of the glaucoma drainage device.

14. An inserter device for use with a glaucoma drainage device including a tube having a proximal end and a distal end with a lumen extending from the proximal end to the distal end, the inserter device comprising:

an elongate handle member having a distal end that defines a stop surface; and a stylus extending beyond the distal end of the elongate handle member, wherein the stylus is sized and configured to be received within the lumen of the glaucoma drainage device with the stop surface interfacing to and limiting proximal movement of the glaucoma drainage device, and wherein the stylus has a first length that extends beyond the stop surface that is less than a second length of a portion of the lumen of the tube of the glaucoma drainage device that extends beyond the stop surface in use;

wherein the elongate handle member includes an orientation marker that is aligned with a bevel on the distal end of the tube of the glaucoma drainage device.

* * * * *